(12) United States Patent
Nadolski

(10) Patent No.: US 11,519,168 B2
(45) Date of Patent: Dec. 6, 2022

(54) VACCINATION GUARD SYSTEM

(71) Applicant: Teresa Nadolski, Troy, IL (US)

(72) Inventor: Teresa Nadolski, Troy, IL (US)

( * ) Notice: Subject to any disclaimer, the term of this patent is extended or adjusted under 35 U.S.C. 154(b) by 0 days.

(21) Appl. No.: 17/346,696

(22) Filed: Jun. 14, 2021

(65) Prior Publication Data

US 2021/0388611 A1     Dec. 16, 2021

Related U.S. Application Data

(60) Provisional application No. 63/038,927, filed on Jun. 15, 2020.

(51) Int. Cl.
    *E04B 2/74*         (2006.01)
    *A61B 90/00*      (2016.01)

(52) U.S. Cl.
CPC .......... *E04B 2/7424* (2013.01); *A61B 90/05* (2016.02); *E04B 2/745* (2013.01); *E04B 2/7435* (2013.01); *E04B 2002/7483* (2013.01)

(58) Field of Classification Search
CPC ........... E04B 2/7424; E04B 2002/7483; E04B 2/7422; E04B 2/7435; E04B 2/745; E04B 2002/747; E04B 2002/7466; A61B 90/05
See application file for complete search history.

(56) References Cited

U.S. PATENT DOCUMENTS

| | | | | |
|---|---|---|---|---|
| 2,915,151 A | * | 12/1959 | Kekenak | E04B 2/7435 |
| | | | | 52/239 |
| 3,265,059 A | * | 8/1966 | Matthews | B25J 21/02 |
| | | | | 135/117 |
| 3,290,847 A | * | 12/1966 | Fenwick | E04B 2/7854 |
| | | | | 52/489.1 |
| 6,210,320 B1 | * | 4/2001 | Rogone | A61G 11/00 |
| | | | | 600/21 |
| 9,038,214 B2 | * | 5/2015 | Hardin | A61G 7/0526 |
| | | | | 5/512 |
| 2002/0038941 A1 | * | 4/2002 | Erickson | A61G 12/001 |
| | | | | 280/651 |
| 2003/0192842 A1 | * | 10/2003 | Suttles | A47B 55/02 |
| | | | | 211/94.01 |

(Continued)

FOREIGN PATENT DOCUMENTS

| | | | | | |
|---|---|---|---|---|---|
| CA | 2239351 A | * | 12/1998 | .......... | E04B 2/7407 |
| CA | 2239351 C | * | 11/2005 | .......... | E04B 2/7407 |

(Continued)

*Primary Examiner* — Phi D A
(74) *Attorney, Agent, or Firm* — Kaspar Law Company LLC; Scott R. Kaspar

(57) ABSTRACT

A guard system is disclosed for protecting patients and medical health professionals from the transmission of airborne contagions during the administration of vaccinations. The system includes a frame having a generally rectangular shape; a transparent sheeting attached to the frame creating a barrier against the transmission of airborne contagions, the sheeting having a front side opposite a back side; an aperture in the transparent sheeting, the aperture sized for administering a vaccination to a patient seated on the back side of the transparent sheeting from the front side; a movable screen portion for covering at least a portion of the aperture; wherein the movable screen portion moves from a closed position to an open position to facilitate the administration of the vaccination.

16 Claims, 5 Drawing Sheets

(56) References Cited

U.S. PATENT DOCUMENTS

| | | | | |
|---|---|---|---|---|
| 2009/0093671 A1* | 4/2009 | Maloney | ............... | A61G 10/005 |
| | | | | 600/21 |
| 2009/0293391 A1* | 12/2009 | DeVore | ................ | A47B 83/001 |
| | | | | 52/745.1 |
| 2016/0194870 A1* | 7/2016 | Oliveira | .................. | E04B 2/789 |
| | | | | 160/369 |
| 2021/0123234 A1* | 4/2021 | Van Kirk | ................... | E04B 1/40 |
| 2021/0322242 A1* | 10/2021 | Hogan | ................. | A61G 10/023 |

FOREIGN PATENT DOCUMENTS

| | | | | | |
|---|---|---|---|---|---|
| EP | 0619108 | A1 | * | 10/1994 | ........... E04B 2/7407 |
| EP | 1462076 | A1 | * | 9/2004 | ............. A61B 46/00 |
| GB | 2424060 | A | * | 9/2006 | ............. A47C 29/00 |
| WO | WO-0222069 | A1 | * | 3/2002 | ........... A61G 10/005 |
| WO | WO-03105575 | A2 | * | 12/2003 | ........... A01K 1/0035 |
| WO | WO-2004081192 | A2 | * | 9/2004 | ........... A47C 29/003 |

* cited by examiner

VACCINATION GUARD SYSTEM

CROSS-REFERENCE TO RELATED APPLICATION

This application claims the benefit of priority to U.S. Provisional Patent Application No. 63/038,927 for a "Vaccination Guard System," filed Jun. 15, 2020, to Teresa Nadolski, which is incorporated by reference in its entirety herein.

TECHNICAL FIELD

The present invention relates to a screen or guard, and more particularly, to a screen system for facilitating vaccinations while protecting the patient and vaccine administrator from airborne contagions.

BACKGROUND

Screens and guards are well known in the art for providing a partial barrier against the transmission of airborne contagions such as common viruses (cold, influenza) and other contagions such as COVID-19, SARS, and the like.

Most typical screens and guards consist of a sheet of transparent material, such as Plexiglass, glass, or a plastic sheeting that separates parties, for example, separating a clerical employee at a desk or counter from the consuming public for which the employee serves.

Vaccinations are routinely administered to patients in open air settings, such as a physician's office, a school gymnasium, a hospital, a local pharmaceutical, and the like. Oftentimes the physician, nurse, pharmacist, or other medical health profession administering the vaccine is in direct contact with the patient, often sitting next to the patient, where airborne contagions can be readily spread from one individual to the other.

Through pandemics such as that involving COVID-19, it has been found that barriers, masks, and distancing between individuals reduces the frequency of transmission of airborne contagions. Currently there is no solution in the art for providing medical health professionals administering vaccinations enhanced protection against airborne contagions other than the use of masks, shields, and similar headgear.

SUMMARY OF THE INVENTION

According to one non-limiting aspect of the present disclosure, a guard system is disclosed for protecting patients and medical health professionals from the transmission of airborne contagions during the administration of vaccinations. The system includes a frame having a generally rectangular shape; a transparent sheeting attached to the frame creating a barrier against the transmission of airborne contagions, the sheeting having a front side opposite a back side; an aperture in the transparent sheeting, the aperture sized for administering a vaccination to a patient seated on the back side of the transparent sheeting from the front side; a movable screen portion for covering at least a portion of the aperture; wherein the movable screen portion moves from a closed position to an open position to facilitate the administration of the vaccination.

According to another non-limiting aspect of the present disclosure, a guard system is disclosed for protecting patients and medical health professionals from the transmission of airborne contagions during the administration of vaccinations. The system includes a frame having a generally rectangular shape; a transparent sheeting attached to the frame creating a barrier against the transmission of airborne contagions, the sheeting having a front side opposite a back side; an aperture in the transparent sheeting, the aperture sized for administering a vaccination to a patient seated on the back side of the transparent sheeting from the front side; a movable screen portion for covering at least a portion of the aperture, the movable screen having a centrally-located opening; wherein the movable screen portion moves from a closed position wherein the opening in the movable screen portion does not align with the aperture in the sheeting to an open position wherein the opening in the movable screen portion is aligned with the aperture in the sheeting, thereby allowing access from the front side of the sheeting through the aperture in the sheeting to the back side of the sheeting.

Additional features and advantages are described herein, and will be apparent from the following Detailed Description and the figures.

BRIEF DESCRIPTION OF THE DRAWINGS

Features and advantages of the system described herein may be better understood by reference to the accompanying drawing, in which.

A skilled artisan will appreciate the foregoing details, as well as others, upon considering the following Detailed Description of certain non-limiting embodiments of the vaccination guard system according to the present disclosure. One of ordinary skill also may comprehend certain of such additional details upon using the system described herein.

DETAILED DESCRIPTION

The present disclosure, in part, is directed to guards and screens, and more particularly, to a guard system for protecting patients and medical health professionals from the transmission of airborne contagions during the administration of vaccinations.

Figure 1:
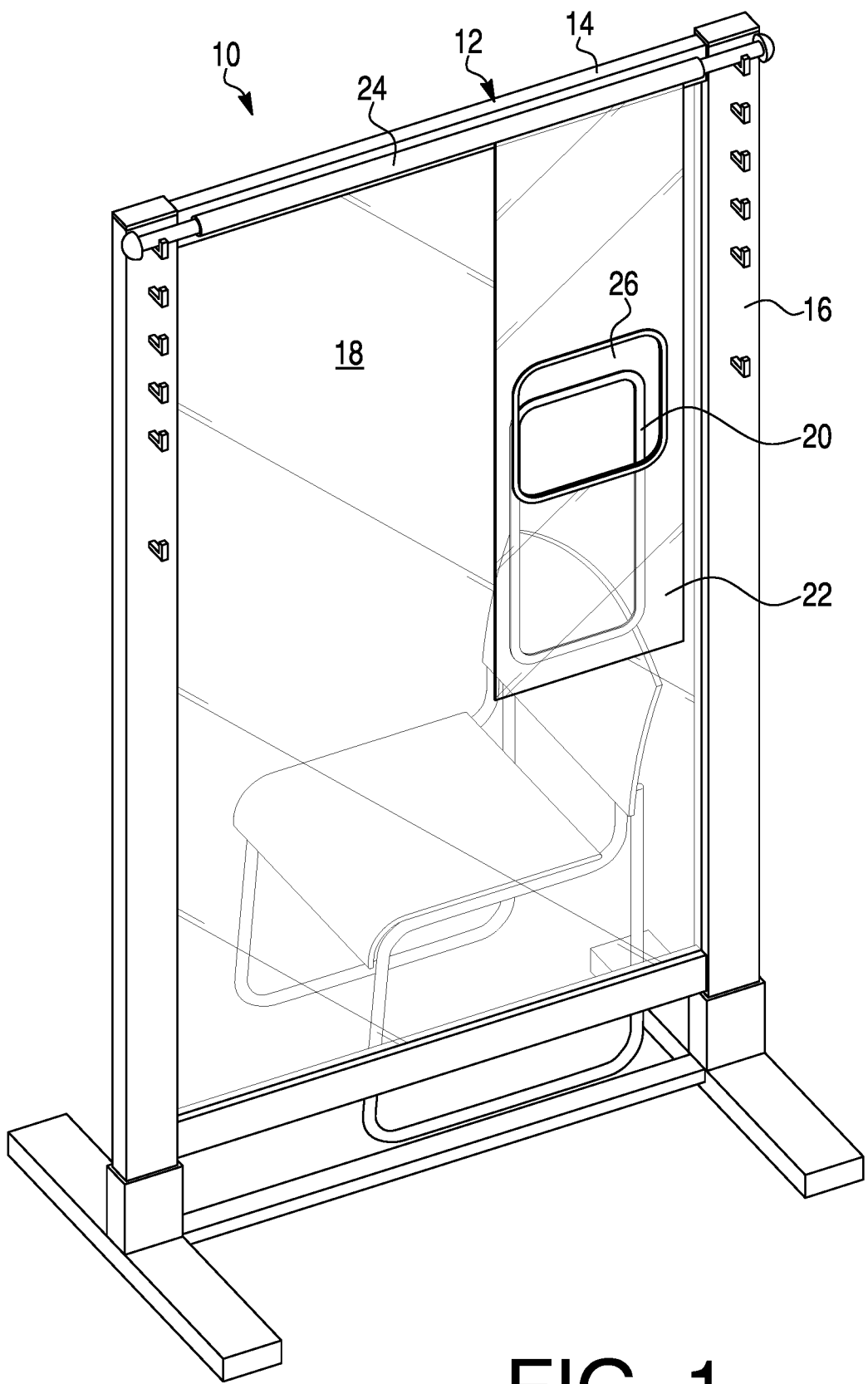
FIG. 1 depicts a perspective view of an embodiment of a guard system of the present disclosure as shown with a movable screen located in a partially open position.

As shown in FIG. 1, a guard system 10 is disclosed, the guard system having a frame 12 with a horizontal portion 14 and vertical sides 16 generally defining a rectangular-shaped structure. Transparent sheeting 18 is attached to the horizontal portion 14 and vertical sides 16 and extends across the frame 12, thereby creating a barrier against the transmission of airborne contagions from a patient-facing side of the sheeting 18 to a medical health professional-facing side of the sheeting opposite the patient-facing side. In this arrangement, a patient sitting on one side of the transparent sheeting 18 would have a physical barrier between the patient and the medical health professional during the administration of vaccinations. Vaccinations may be administered via an aperture 20 in the sheeting 18, the aperture generally rectangular-shaped and sized and located to provide the medical health professional with access to a patient's upper arm.

A movable screen 22 affixed to a support bar 24 can be raised or lowered to partially or entirely close the aperture 20 in the sheeting 18. As shown in FIG. 1, the movable screen 22 is located in a partially open position allowing access to a patient via aperture 20 for the administration of a vaccination.

Movable screen 22 and sheeting 18 are composed of a transparent material such that individuals on opposite sides of the movable screen and sheeting may see one another, and in the situation of a medical health professional vaccinating a patient, to permit the medical health professional to adequately see the patient and the patient's arm and/or the situs of the vaccination on the patient's body. Movable screen and sheeting may be made of glass, a plastic or polymer sheeting, or a translucent vinyl material, as non-limiting examples. In one embodiment of the present invention, movable screen 22 and sheeting 18 are made of a sturdy plastic sheeting, such as Plexiglass® brand plastic sheeting.

Figure 2:
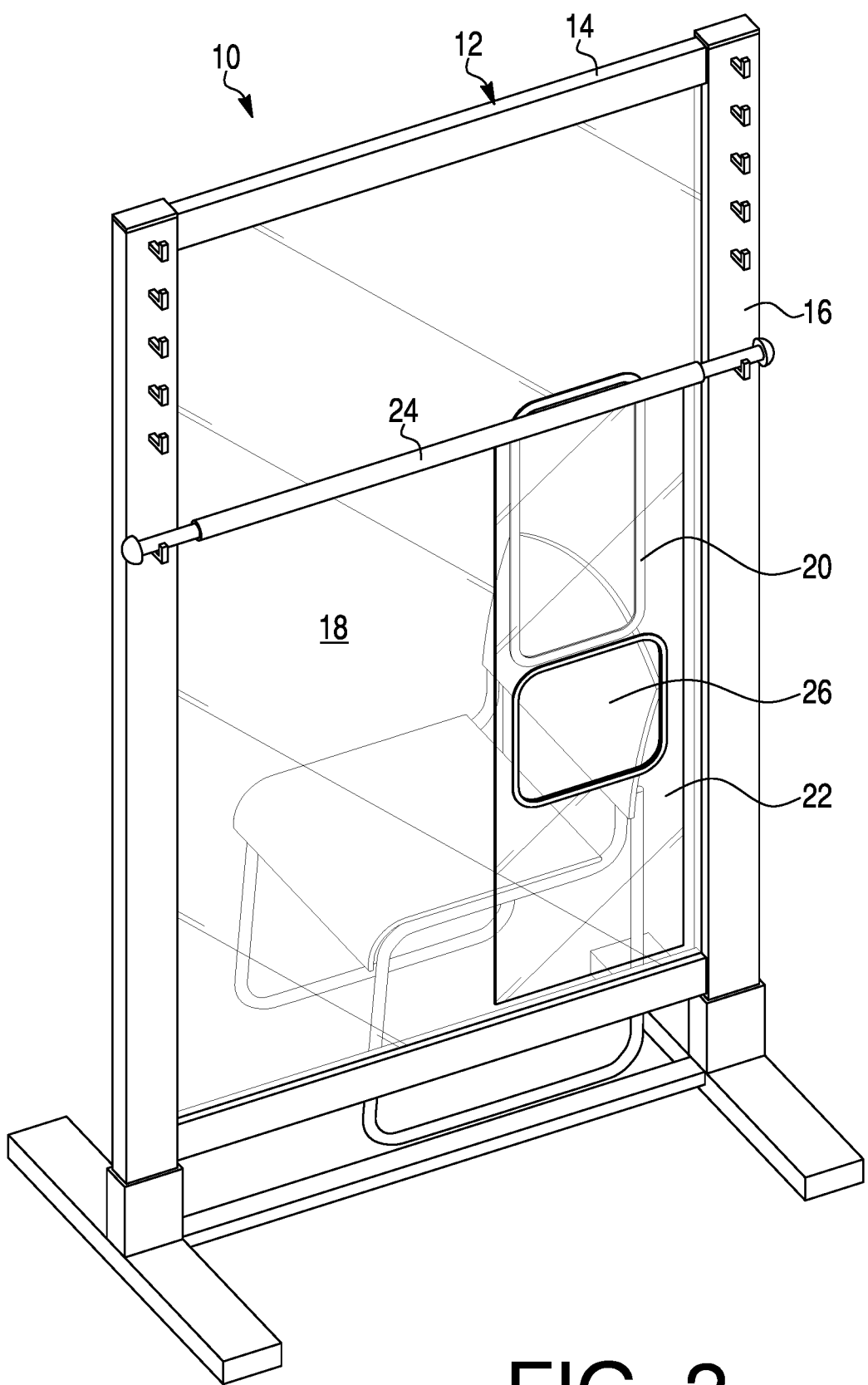
FIG. 2 depicts a perspective view of an embodiment of a guard system of the present disclosure as shown with a movable screen located in a closed position.

As shown in FIG. 2, the movable screen 22 is located in a closed position, thereby closing off the aperture 20 in the sheeting 18. Such a closed position may be desirable to allow the medical health professional to prepare for the administration of the vaccination while maintaining a physical barrier between the medical health professional and the patient. At such time when the administration of the vaccination is to commence, the medical health professional may raise the movable screen 22 to the open position such that aperture 20 is uncovered.

Figure 3:
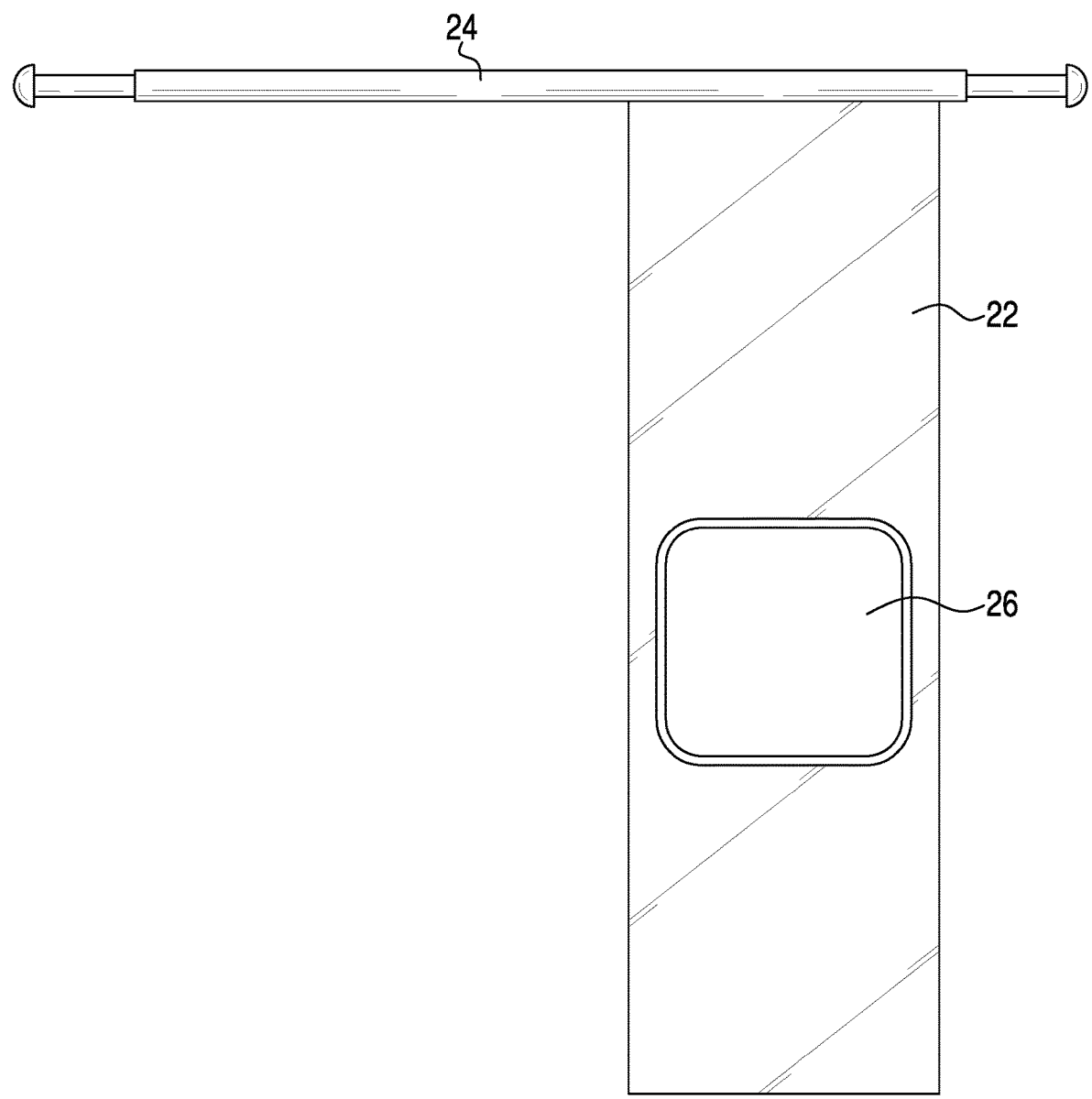
FIG. 3 depicts a front view of the movable screen of FIGS. 1 and 2.

As shown in FIG. 3, the movable screen 22 is attached to support bar 24, the attachment of which may be by tape, an adhesive, or another physical connector such as a screw, staple, nails, and the like. An opening 26 is located approximately centrally on the screen 22, the opening 26 configured to align with at least a portion of the aperture 20 in the sheeting 18 when the screen 22 is placed onto the frame 12.

Figure 4:
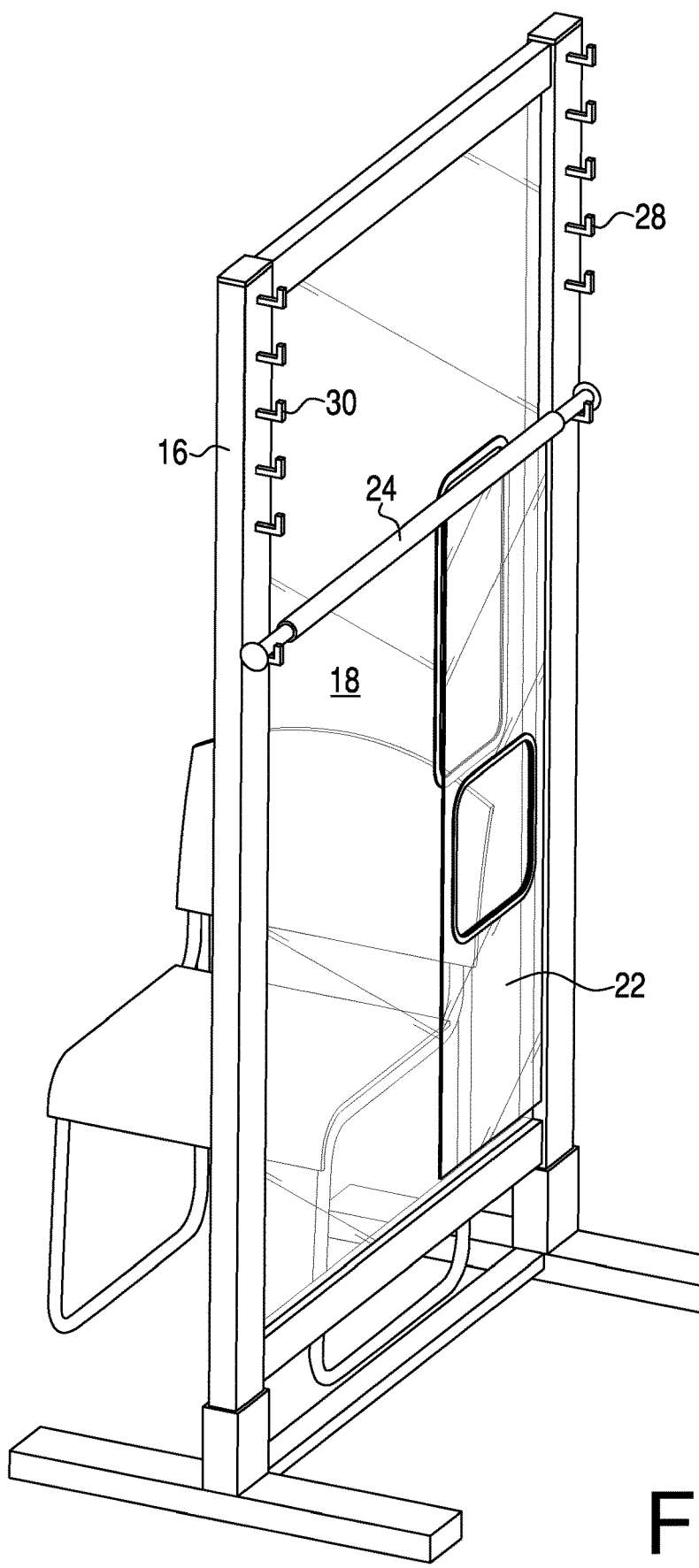
FIG. 4 depicts a detailed view of a latching mechanism of the guard system depicted in FIG. 2.

As shown in FIG. 4, the support bar 24 of the movable screen 22 is retained by a plurality of hooks or supporting members 28, 30, which are interconnected with vertical sides 16 to define the open and closed positions of the movable screen 22, including a plurality of intermediary positions providing for partial opening of the movable screen 22.

Figure 5:
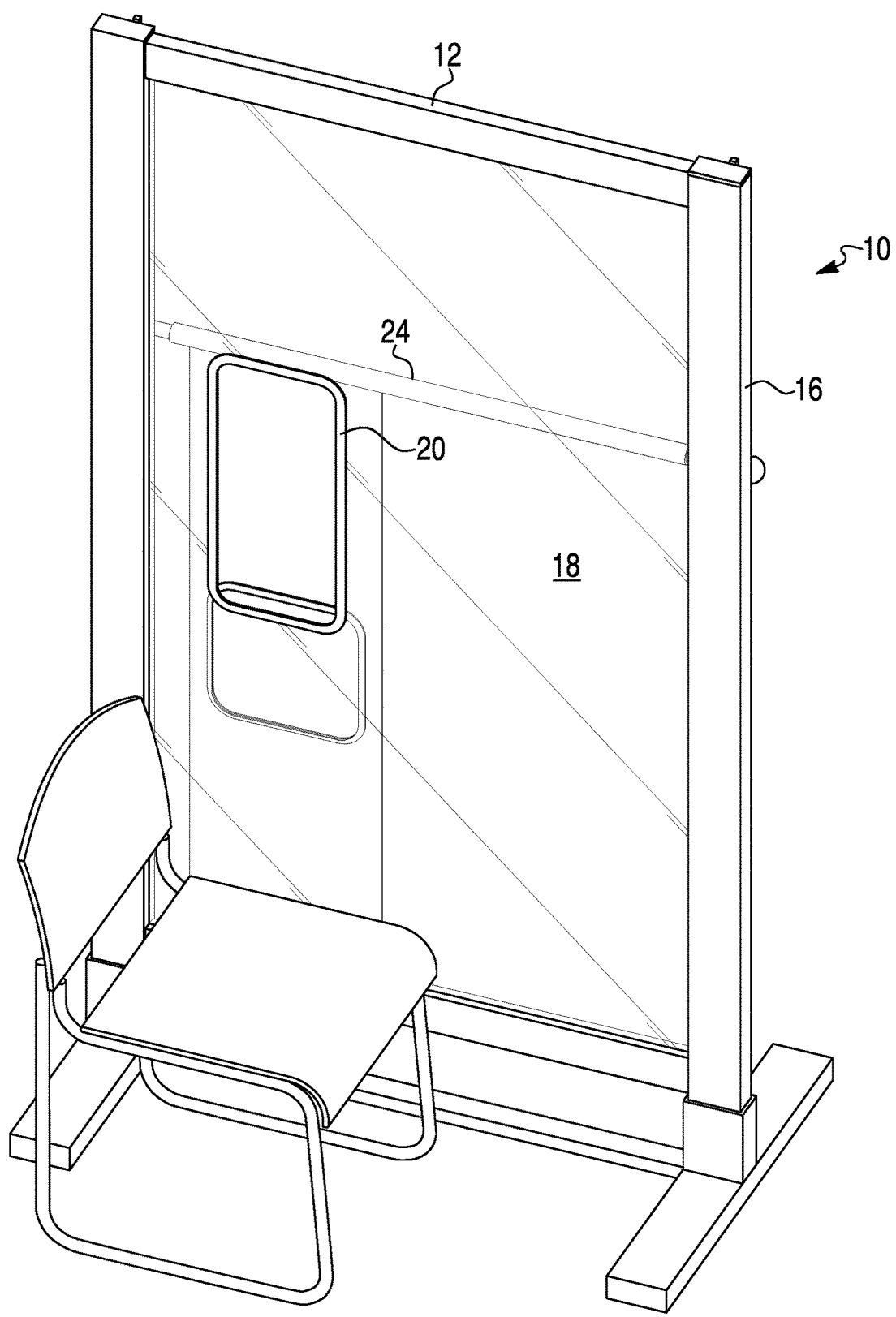
FIG. 5 depicts the guard system depicted in FIG. 2 from the perspective view of a patient.

As shown in FIG. 5, the guard system 10 of the present disclosure has a patient-facing side in which the patient would be seated in a chair positioned proximate to the aperture 20. In use, the movable screen 22 would be in a closed position upon seating of the patient in the chair, allowing for the medical health professional to prepare for the vaccination administration, as well as allowing the patient to reposition or remove clothing to expose the patient's upper arm for receiving the vaccination. At such time when the medical health professional is ready to deliver the vaccination, the movable screen 22 may be raised to an open position, allowing for aperture 20 to be uncovered such that the medical health professional may reach through the aperture to administer the vaccination into the patient's upper arm.

In use, the guard system 10 provides protection from airborne contagions, such as the common cold, influenza, or COVID-19, among others, to individuals residing on either side of the frame 12. This is accomplished by use of the sheeting 18 positioned in between a patient and the medical health professional, and the aperture 20 in the sheeting 18 allows for the medical health professional to have deliberate contact with the patient when necessary to carry out the vaccination process. Specifically, movable screen 22, when positioned to cover the aperture 20, maintains an effective barrier between the patient and the medical health professional. When the medical health professional desires to conduct the vaccination, the professional raises the movable screen 22 to an open or partially open position, such that the aperture 20 in the sheeting 18 is revealed or at least partially revealed, as the medical health professional may determine or desire.

Alternatively, the movable screen portion 22 also may have an opening 26. As the movable screen 22 is raised or lowered by the medical health professional, the opening 26 also moves upwardly or downwardly, such that it may align partially or completely with the aperture 20 in the sheeting 18. When the opening 26 in the movable screen 22 is fully aligned with the aperture 20 in the sheeting 18, then the medical health professional may easily pass his or her hand through the opening 26 and through the aperture 20 to reach the patient for administering a vaccination. After the vaccination process, the medical health professional may lower the movable screen 22 such that the opening 26 in the movable screen 22 no longer is aligned with the aperture 20 in the sheeting 18, once again sealing off the sheeting 18 such that airborne contagions do not pass directly through the opening or the aperture from one person to the other.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended set of claims.

What is claimed is:

1. A vaccination guard system comprising:
   a frame having a generally rectangular shape, the frame having a plurality of supporting members, the supporting members comprise at least a pair of hooks secured to the frame;
   a transparent sheeting attached to the frame creating a barrier against the transmission of airborne contagions, the sheeting having a front side opposite a back side;
   an aperture in the transparent sheeting, the aperture sized for administering a vaccination to a patient seated on the back side of the transparent sheeting from the front side;
   a movable screen portion for covering at least a portion of the aperture, wherein the movable screen portion is comprised of a rectangular shaped sheeting attached to a support bar that is received by the plurality of supporting members on the frame;
   wherein the movable screen portion moves from a closed position to an open position to facilitate the administration of the vaccination.

2. The system of claim 1 wherein the supporting members are positioned along the length of the frame to provide for at least two vertical positions of the movable screen portion when the support bar of the movable screen portion is received by at least one of the supporting members.

3. The system of claim 2 wherein a first vertical position of the movable screen portion provides for the movable screen portion to be covering the aperture in the transparent sheeting.

4. The system of claim 2 wherein the second vertical position of the movable screen portion provides for the movable screen portion to be vertically above the aperture in the transparent sheeting.

5. A vaccination guard system comprising:
a frame having a generally rectangular shape;
a transparent sheeting attached to the frame creating a barrier against the transmission of airborne contagions, the sheeting having a front side opposite a back side;
an aperture in the transparent sheeting, the aperture sized for administering a vaccination to a patient seated on the back side of the transparent sheeting from the front side;
a movable screen portion for covering at least a portion of the aperture, the movable screen having a centrally-located opening;
wherein the movable screen portion moves from a closed position wherein the opening in the movable screen portion does not align with the aperture in the sheeting to an open position wherein the opening in the movable screen portion is aligned with the aperture in the sheeting, thereby allowing access from the front side of the sheeting through the aperture in the sheeting to the back side of the sheeting.

6. The system of claim 5 wherein the movable screen portion is comprised of a rectangular shaped sheeting attached to a support bar.

7. The system of claim 6 wherein the support bar of the movable screen portion is configured to be received by the frame.

8. The system of claim 7 wherein the frame has a plurality of supporting members for receiving and holding the support bar of the movable screen portion against the frame.

9. The system of claim 8 wherein the supporting members comprise at least a pair of hooks secured to the frame.

10. The system of claim 8 wherein the supporting members are positioned along the length of the frame to provide for at least two vertical positions of the movable screen portion when the support bar of the movable screen portion is received by at least one of the supporting members.

11. The system of claim 10 wherein a first vertical position of the movable screen portion provides for the movable screen portion to be covering the aperture in the transparent sheeting.

12. The system of claim 10 wherein the second vertical position of the movable screen portion provides for the movable screen portion to be vertically above the aperture in the transparent sheeting.

13. A vaccination guard system comprising:
a frame having a generally rectangular shape, the frame having a top opposite a bottom that are connected by a pair of upright sides;
a transparent sheeting attached to the top, bottom, and sides of the frame to create a barrier against the transmission of airborne contagions, the sheeting having a front side opposite a back side;
an aperture in the transparent sheeting, the aperture sized for administering a vaccination to a patient seated on the back side of the transparent sheeting from the front side;
a plurality of hooks disposed in the sides of the frame;
a movable screen portion for covering at least a portion of the aperture, the movable screen supported by and suspended from at least one of the plurality of hooks, the movable screen further having a centrally-located opening;
wherein the movable screen portion moves from a closed position wherein the opening in the movable screen portion does not align with the aperture in the sheeting to an open position wherein the opening in the movable screen portion is aligned with the aperture in the sheeting, thereby allowing access from the front side of the sheeting through the aperture in the sheeting to the back side of the sheeting.

14. The system of claim 13 wherein the movable screen portion is comprised of a rectangular shaped sheeting attached to a support bar.

15. The system of claim 14 wherein the hooks disposed within the sides of the frame are configured to receive the support bar.

16. The system of claim 15 wherein the movable screen is moved to an open position by raising the movable screen with respect to the frame, the support bar of the movable screen received by another of the plurality of hooks disposed within the sides of the frame.

* * * * *